United States Patent [19]

Kohno et al.

[11] 4,326,252
[45] Apr. 20, 1982

[54] METHOD OF RECONSTRUCTING CROSS-SECTION IMAGE

[75] Inventors: Hideki Kohno, Tokyo; Hidemi Shiono, Akikawa; Shinji Yamamoto, Hachioji, all of Japan

[73] Assignee: Hitachi Medical Corporation, Tokyo, Japan

[21] Appl. No.: 101,769

[22] Filed: Dec. 10, 1979

Related U.S. Application Data

[63] Continuation of Ser. No. 854,672, Nov. 25, 1977, abandoned.

[30] Foreign Application Priority Data

Nov. 29, 1976 [JP] Japan .............................. 51-142256

[51] Int. Cl.³ ............................................ G01N 23/00
[52] U.S. Cl. .................................. 364/414; 250/336; 250/445 T; 358/111
[58] Field of Search .............. 364/414, 515, 576, 819, 364/826, 827; 250/445 T, 336, 362; 358/111, 160, 166

[56] References Cited

U.S. PATENT DOCUMENTS 3,153,207 10/1964 Brown .................................. 358/166
3,924,129 12/1975 LeMay ................................ 250/336
3,936,636  2/1976 Percival ........................... 250/445 T Primary Examiner—Errol A. Krass
Attorney, Agent, or Firm—Craig and Antonelli

[57] ABSTRACT

A method is disclosed in which projection images of a certain cross-section of an object are produced through irradiation from various directions to the cross-section, and a three-dimensional image of the cross-section is reconstructed from the projection images. A convolution integral operation is performed on the projection images by means of a weighting function obtained from a function whose second differentiation is positive in at least a predetermined range of a spacial frequency domain and which has a positive first-differential coefficient at a point where the spacial frequency is equal to zero.

7 Claims, 10 Drawing Figures

F I G. 8
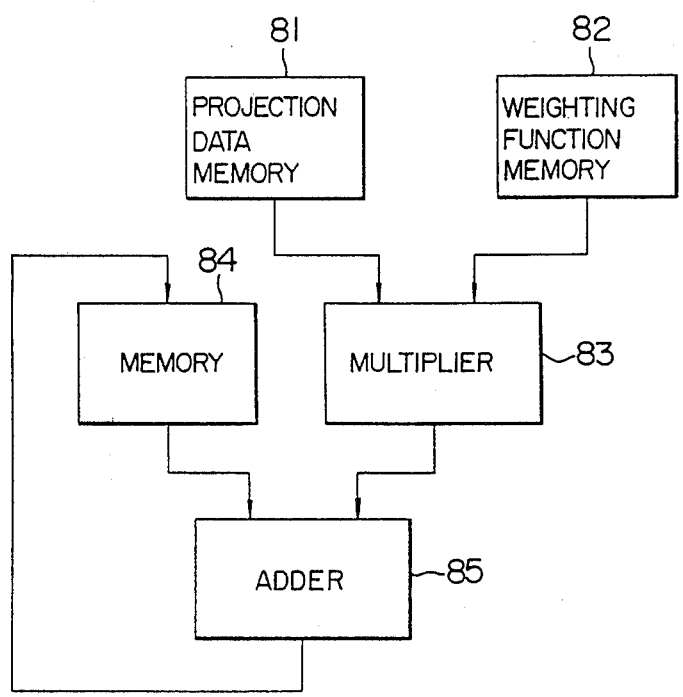

METHOD OF RECONSTRUCTING CROSS-SECTION IMAGE

This is a continuation of application Ser. No. 854,672, filed Nov. 25, 1977, now abandoned.

This invention relates to a method of reconstructing a cross-section or tomographic image of an object from projection images produced through irradiation from various directions to the cross-section and in particular to such a method using a convolution integral operation for the reconstruction.

The invention will be better understood from the following description made in comparison with the prior art methods with the aid of the accompanying drawings, in which:

FIG. 8 is a block diagram of a processor unit for performing a convolution integral operation.

An apparatus for reconstructing a cross-section image of an object from projection images has been applied to X-ray apparatuses and is indispensable for medical diagnoses. The detection of the projection images in such apparatuses has been known, for example, in U.S. Pat. No. 3,778,614 (corresponding to British Pat. No. 1,283,915). A principle for reconstructing a cross-section image as adopted in such apparatuses is disclosed in an article entitled "Three-Dimensional Reconstruction From Radiographs And Electron Micrographs: applications of convolutions instead of Fourier transforms" by G. N. Ramachandran et al. in Proc. Nati. Acad. USA, 68, September 1971, pp. 2236-2240, and is often referred to as the convolution method, which will be herein briefly reviewed in conjunction with FIG. 1.

Figure 1:
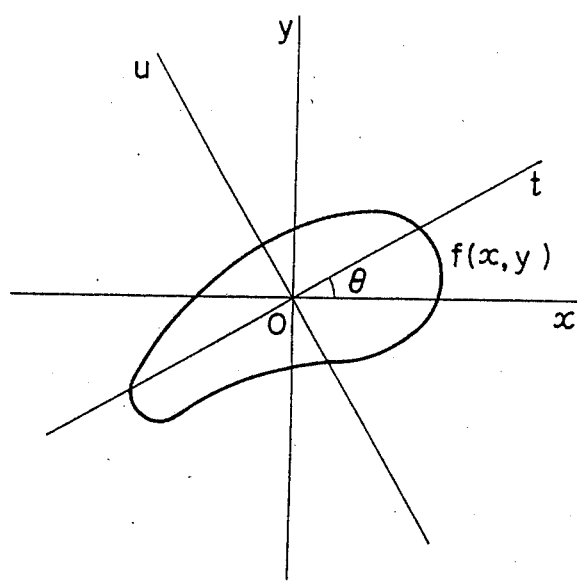
FIG. 1 shows a coordinate system to illustrate the principle of the invention.

Referring to FIG. 1, assuming that an image f(x, y) defined in a x-y plane is projected to a t-axis inclined from the x-axis by an angle $\theta$, then the projection image p(t, $\theta$) can be given by the following equation:

$$p(t, \theta) = \int_{-\infty}^{\infty} f(x,y) \, du \tag{1}$$

wherein $t = x \cos \theta + y \sin \theta$ and $u = -x \sin \theta + y \cos \theta$. The projection image p(t, $\theta$) is a quantity which is actually determined through an analysis apparatus. The most important problem is how to construct the real cross-section image f(x, y) from the actually available projection image p(t, $\theta$). The equation (1) may be transformed into the following equation:

$$f(x,y) = \frac{1}{4\pi^2} \int_0^\pi d\theta \int_{-\infty}^\infty \hat{p}(\omega, \theta) \tag{2}$$
$$\times \exp\{j\omega(x \cos \theta + y \sin \theta)\} X |\omega| \, d\omega$$

wherein $\hat{p}(\omega, \theta)$ represents a function derived from the projection image p(t, $\theta$) through Fourier transform and $\omega$ is referred to as spacial frequency which represents a spacial quantity in terms of frequency and time. For example, it is assumed that line segments drawn with the intervals of a mm have a spacial frequency component of $2\pi/a$ ($\pi = 3.141592 \ldots$). In other words, the quantity $\omega$ may be considered as representing a fineness of a geometrical figure. Thus, a geometrical figure having a high frequency component means that the figure has a correspondingly fine resoluble pattern. The above equation (2), which gives a base for reconstructing a cross-section image of an object from projection images produced through irradiation from various directions, is discussed in detail in the above article of G. N. Ramachandran et al. Accordingly, further description will be unnecessary.

The equation (2) is to be rewritten in a form of convolution. The equation (2) may be considered as an inverse Fourier transform of a product of the Fourier-transformed functions $\hat{p}(\omega, \theta)$ and $|\omega|$. Now, a function $\phi(t)$ is defined as follows:

$$\phi(t) = \frac{1}{2\pi} \int_{-\infty}^\infty \omega \exp(j\omega t) d\omega \tag{3}$$

$$\hat{\phi}(t) = \int_{-\infty}^\infty \phi(t) \exp(-j\omega t) d\omega = |\omega| \tag{3'}$$

Namely, $\phi(t)$ is a function derived from the inverse Fourier transform of $|\omega|$. From the equations (3) and (3'), the equation (2) can be transformed as follows:

$$f(x, y) = \frac{1}{4\pi^2} \int_0^\pi d\theta \int_{-\infty}^\infty \hat{p}(\omega, \theta) \hat{\phi}(\omega)$$
$$\times \exp\{j\omega(x \cos \theta + y \sin \theta)\} d\omega$$

Hence, $$f(x, y) = \frac{1}{4\pi^2} \int_0^\pi d\theta \int_{-\infty}^\infty p(t - \tau, \theta)\phi(\tau) d\tau \tag{4}$$

Figure 2:
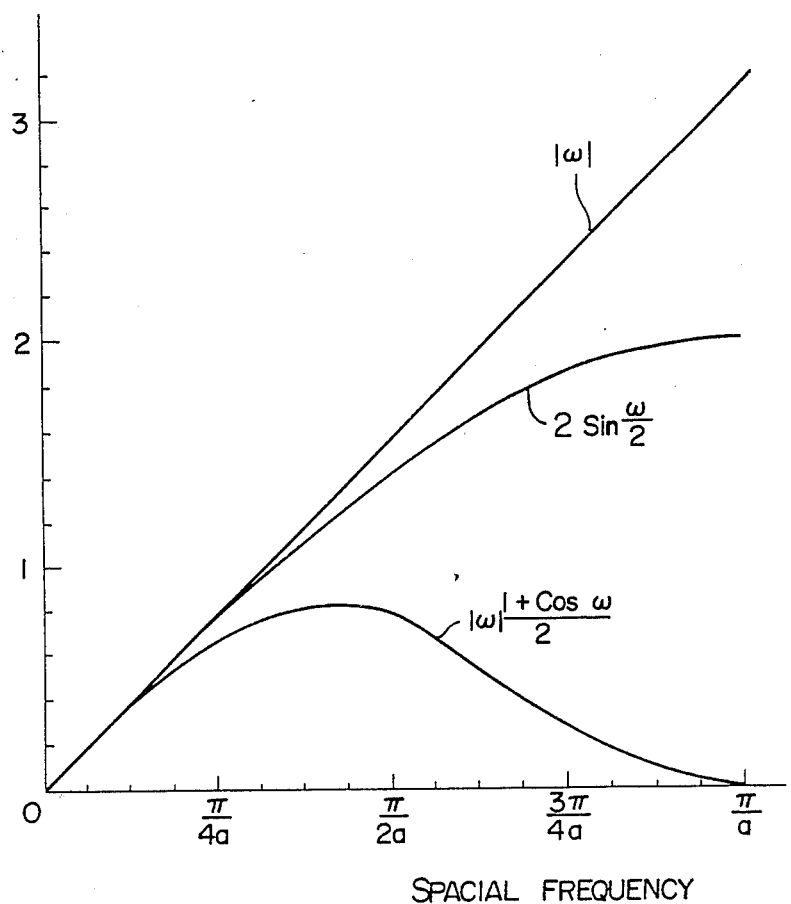
FIG. 2 is a graph to illustrate spacial frequency characteristics of weighting functions conventionally employed.

In the equation (4), the inner integral is known as so-called convolution integral, wherein $\phi(\tau)$ is referred to as a weighting function. The equation (4) provides an algorithm for reconstructing the cross-section image from the projection images, as is referred to as the convolution method. The weighting function $\phi(\tau)$ of the equation (4) will exert a great influence on the quality of the reconstructed image. There have hitherto been proposed several weighting functions. In addition to $|\omega|$ which is necessarily derived through mathematic procedures as described above, typical examples include the inverse Fourier transforms of functions $2 \sin \omega/2$, $|\omega|(1+\cos \omega)/2$, etc. which are made free of high frequency components caused by vibrations of some portions such as bones of human body. FIG. 2 graphically illustrates curves of these typical weighting functions in the spacial frequency domain. It can be seen that all of the first differential coefficients of these functions are equal to 1 at $\omega=0$, while the coefficients are equal to or smaller than 1 at $\omega \neq 0$.

Though the inventors have tried to reconstruct cross-section images from absorption data (corresponding to the projection images) available from an actual X-ray apparatus by using the weighting functions having spacial frequency characteristics such as illustrated in FIG. 2, it has been found that the reconstructed images are too blurred to be used for practical purposes.

Accordingly, an object of the invention is to provide a cross-section or tomographic image reconstruction method which assures the reconstruction of an image having substantially no blurs.

According to the present invention, there is provided a method of reconstructing a cross-section image, comprising a step of irradiating a cross-section of an object with radiation rays from plural directions, a step of detecting the radiation rays through said object to obtain a signal of plural projection images of said cross-section produced through the irradiation, and a step of performing a convolution integral operation on said signal by means of a weighting function to reconstruct a three-dimensional image of said cross-section, wherein said weighting function is an inverse Fourier transform of a function whose second differentiation is positive in at least a predetermined range of a spacial frequency domain and which has a positive first-differential coefficient at a point where the spacial frequency is equal to zero.

Before entering into detailed description of the weighting functions employed in the cross-section image reconstruction method according to the invention, the cause which gives rise to the blurs in the reconstructed image will be first described on the basis of the experimental analyses conducted by the inventors. In brief, the blurs of the reconstructed images are ascribable to the fact that irradiation X-ray has inevitably a certain line spread in any practical X-ray apparatus. More particularly, it is difficult from the technical standpoint to obtain sharply focussed or thin X-ray. Further, even when a thin X-ray can be produced, inherent quantum noise of the X-ray will then increase since the amount of X-ray incident on an X-ray detector is decreased. The quantum noise is statistical fluctuations in the amount of X-ray and inevitably occurs in the processing of X-ray. When the amount of X-ray is increased by a factor N, the corresponding increase of the quantum noise will be by a factor $\sqrt{N}$, so that the signal-to-noise ratio is improved. Accordingly it is rather preferred in practice to employ a somewhat weakly focussed or thick X-ray so as to reduce the noise in the reconstructed image, while blur due to the spread of the thick X-ray is to be compensated in the course of image reconstruction process. The blur of the reconstructed image ascribable to the spread of X-ray may be explained as described below.

Figure 3:
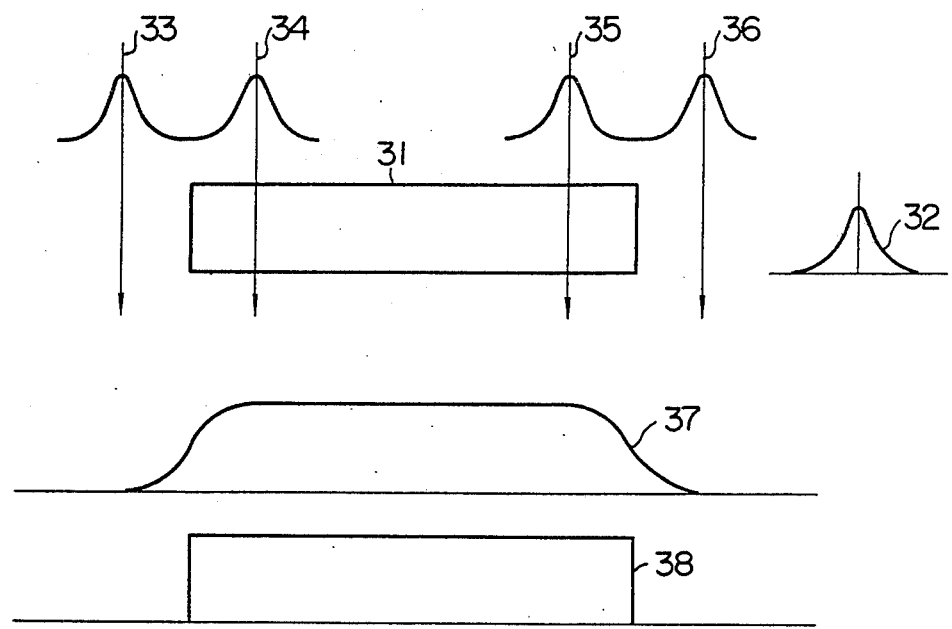
FIG. 3 illustrates graphically a cause of blurs produced in the reconstructed image.

It is assumed that a rectangular object 31 such as shown in FIG. 3 is to be analyzed. When a X-ray traverses across the rectangular object 31, absorption of X-ray by the object 31 will occur. The spread of X-ray is of such a form as indicated by a curve 32. The X-ray absorption by the object 31 will begin to increase at a position 33 and continue to increase until a position 34 has been attained after the leftward displacement of the X-ray as viewed in FIG. 3. In the region between the positions 34 and 35, the X-ray absorption will remain to be constant. After passing by a position 35, the X-ray absorption will begin to be decreased and become zero at a position 36. Thus, the X-ray absorption may be plotted as a curve 37 in dependence on the X-ray irradiation positions. The curve 37 may be considered as a blurred image of a sharp or well-defined projection image 38.

Now, referring again to the equation (1), it is assumed that p(t, $\theta$) represents a projection image having no blur and $\psi(t)$ represents the spread of X-ray. Then, the actually measured projection image Q(t, $\theta$) may be given by convolution integral of p(t, $\theta$) and $\psi(t)$, as expressed as follows:

$$Q(t, \theta) = \int_{-\infty}^{\infty} p(t - \tau, \theta)\psi(\tau)d\tau \tag{5}$$

When both terms of the equation (5) undergo Fourier transform, the convolution is given in a form of a product. Namely, $$\hat{Q}(\omega,\theta)=\hat{p}(\omega,\theta)\hat{\psi}(\omega) \tag{6}$$

wherein $\hat{Q}(\omega, \theta)$, $\hat{p}(\omega, \theta)$ and $\hat{\psi}(\omega)$ represent, respectively, Fourier transforms of the functions Q(t, $\theta$), p(t, $\theta$) and $\psi(t)$. From the equation (6), p($\omega$, $\theta$) can be determined as follows:

$$p(\omega, \theta) = \frac{\hat{Q}(\omega, \theta)}{\hat{\psi}(\omega)} \tag{7}$$

Thus, the equation (2) can be rewritten as follows:

$$f(x, y) = \frac{1}{4\pi^2} \int_{-\infty}^{\infty} \hat{Q}(\omega, \theta) \cdot \frac{|\omega|}{\hat{\psi}(\omega)} \tag{8}$$
$$\times \exp\{j\omega(x \cos \theta + y \sin \theta)\}d\omega$$

For transforming the equation (8) into the convolution integral form, $\phi(t)$ is defined as $$\phi(t) = \int_{-\infty}^{\infty} \frac{|\omega|}{\hat{\psi}(\omega)} \exp(j\omega t)d\omega \tag{9}$$

Thus, the equation (8) can be rewritten in the following convolution integral form:

$$f(x, y) = \frac{1}{4\pi^2} \int_0^{\pi} d\theta \int_{-\infty}^{\infty} Q(t - \tau, \theta)\phi(\tau)d\tau \tag{10}$$

Figure 4:
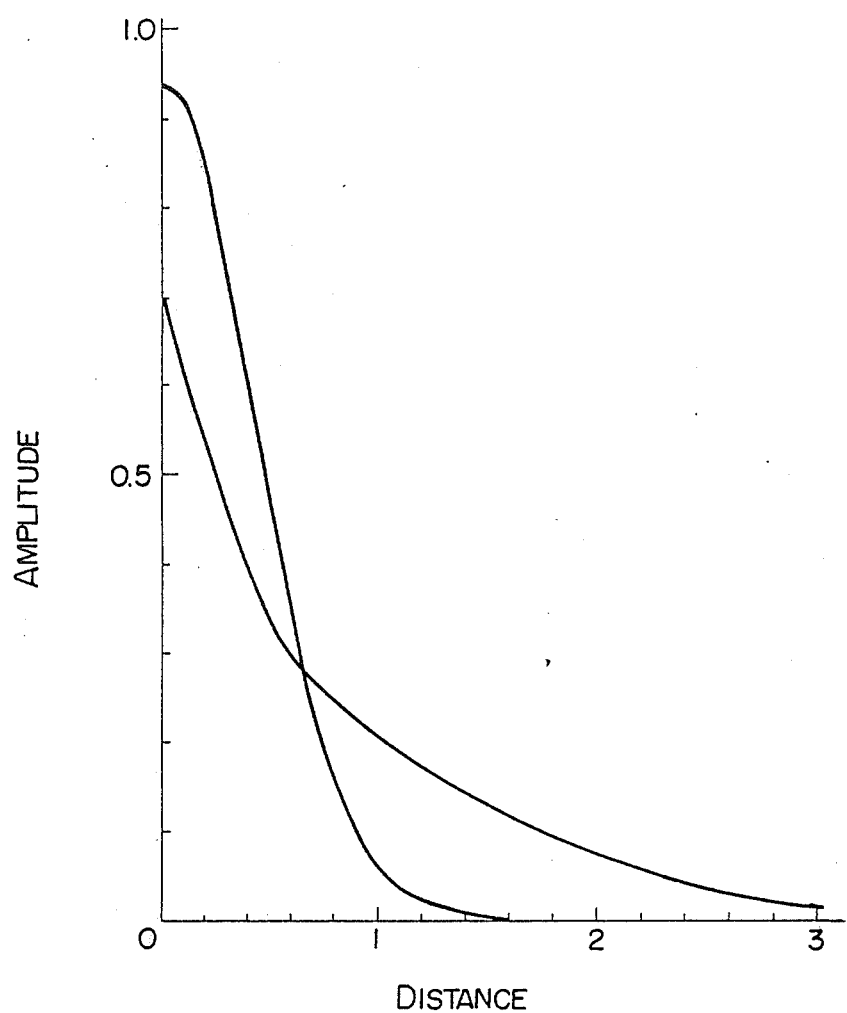
FIG. 4 illustrates graphically a typical line spread of an X-ray.

It is a well known fact that the line spread function $\psi(t)$ can be given by a Gaussism function or an exponential function and takes forms such as illustrated in FIG. 4. Fourier transformation of this function will generally result in a monotone decreasing function of the spacial frequency $\omega$, as is well known in the art. Consequently, the function given by the reciprocal of $\hat{\psi}(\omega)$ will increase monotonously over the spacial frequency $\omega$. Thus, the second differentiation or second-derived function of $|\omega|/\hat{\psi}(\omega)$ will be positive over $\omega$. When the weighting function having such spacial frequency characteristics is used, the high frequency components will become intensified in the reconstructed image, involving an image of a sharp contour. Further, it is a necessary condition for the image reconstruction that the first differential coefficient of the weighting function of the spacial frequency domain should take a positive value at $\omega=0$, as is apparent from the equation (2). Thus, in order to have a cross-section image having no blur to be reconstructed from the projection images having blurs, the weighting function should have such a profile in the spacial frequency domain of the projection image that the first differential coefficient takes a positive value at $\omega=0$ and the second differentiation is positive over $\omega$.

Figure 5:
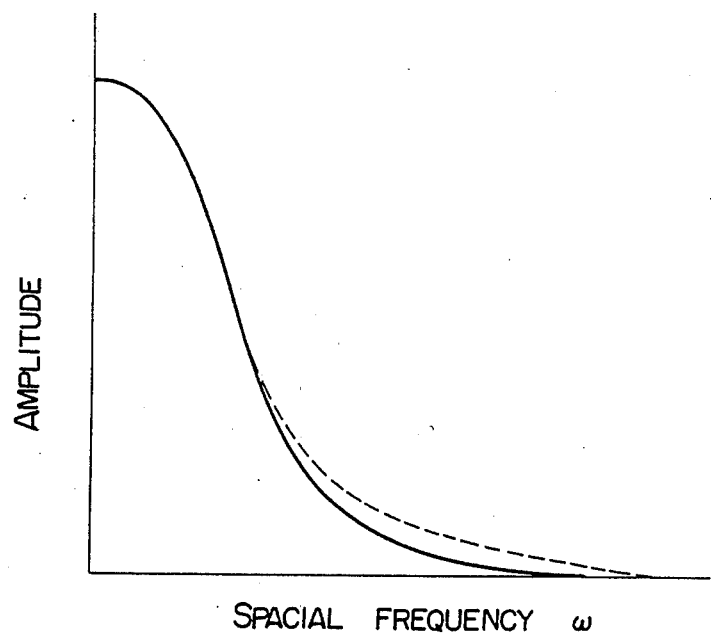
FIG. 5 illustrates graphically difference in the spacial frequency characteristics of a blurred image and a sharp image.
Figure 6:
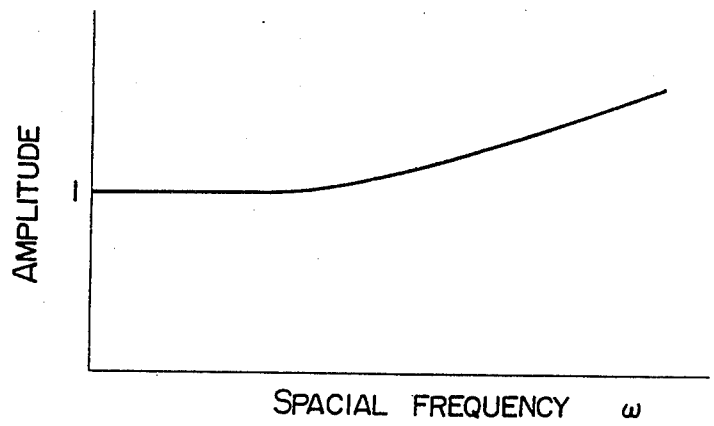
FIG. 6 illustrates graphically a deblurring spacial frequency characteristic.

With a view to determining how the projection images 37 and 38 differ from each other, analysis is made in respect of the spacial frequency components of these projection images after Fourier transform thereof. Referring to FIG. 5, a solid line curve represents the Fourier transform of the projection image 37, while a broken line curve represents that of the projection image 38. As can be seen from the graphical representation of FIG. 5, the significant difference between the images 37 and 38 can be found in respect of the contents of high frequency components. More particularly, as the high frequency component is increased in the spacial frequency components of a projection image, the blur will become more remarkable. It will be readily appreciated from FIG. 5 that, in order to obtain the spacial frequency characteristic represented by the broken line curve from the solid line spacial frequency characteristic, the latter should be corrected by combining multiplicatively with a spacial frequency characteristic such as represented by the curve shown in FIG. 6. The spacial frequency characteristic curve shown in FIG. 6 has an amplitude remaining constant at 1 in a low frequency range and progressively increasing in a high spacial frequency range. Consequently, a combined or synthesized curve resulted from the spatial frequency characteristic represented by the solid line curve shown in FIG. 5 multiplied with the curve shown in FIG. 6 will remain substantially the same as the former in the low frequency range and approximate to the broken line curve shown in FIG. 5 in the high frequency range. In this manner, a projection image having no blur can be obtained through reverse Fourier transformation of the spacial frequency function represented by the solid line curve in FIG. 5.

As described hereinbefore, the reconstruction of a cross-sectional image is effected through the convolution method in which a weighting function having a frequency characteristic of $|\omega|$ is used. Accordingly, in order to suppress the blur in the image reconstruction process, such a weighting function should be used in which $|\omega|$ is combined multiplicatively with a function representing the spacial frequency characteristic shown in FIG. 6.

Thus, according to the teaching of the invention, there is proposed a cross-sectional image reconstruction method through convolution, wherein a weighting function is used which has such a profile in the spacial frequency domain that the first differential coefficient thereof takes a positive value at $\omega=0$ and the second differentiation is positive over the spacial frequency $\omega$.

In accordance with another aspect of the invention, a weighting function is used which has such a profile in the spacial frequency domain of the projection image that the first differential coefficient thereof takes a positive value at $\omega=0$, the second differentiation is positive until a predetermined value of $\omega$ and the function decreases in the frequency range beyond the predetermined value of $\omega$, thereby to compensate for the influence of the quantum noise of an X-ray described hereinbefore.

Figure 7:
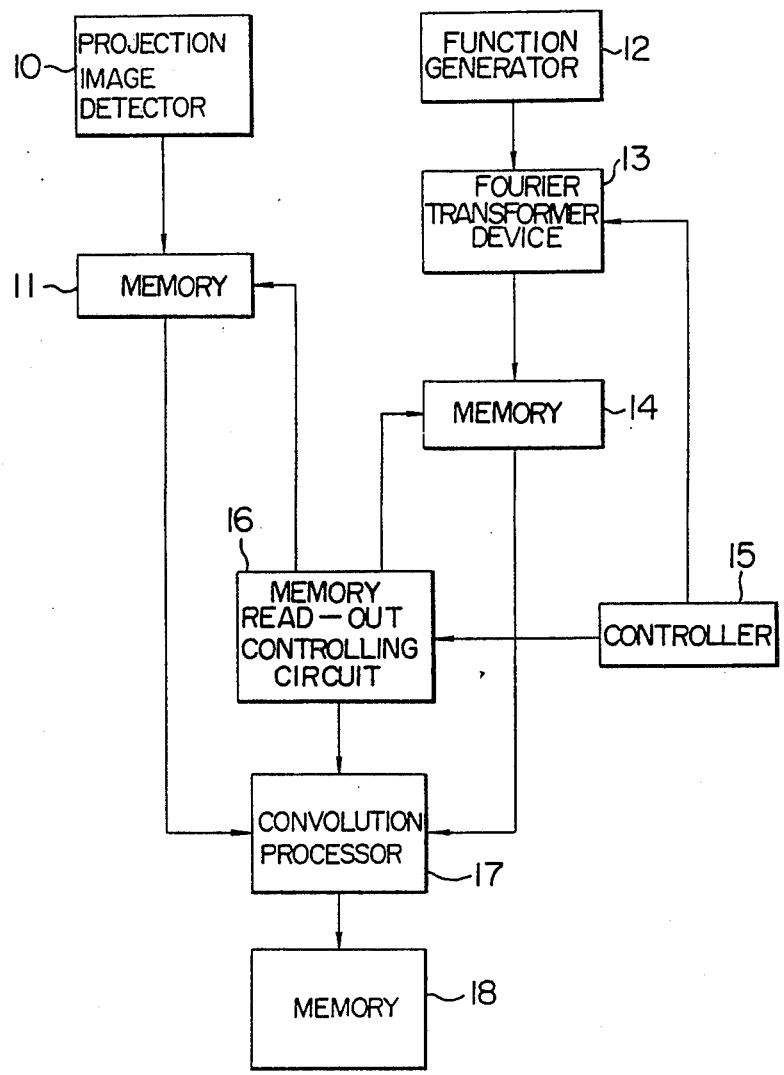
FIG. 7 is a block diagram to show an apparatus for carrying out the invention.

FIG. 7 is a block diagram showing an apparatus for carrying out the cross-section image reconstruction method according to the invention. In the figure, reference numeral 10 denotes a projection image detector which may be constituted by a conventional X-ray tomography apparatus. Data obtained from the projection image detector 10 are stored in a memory 11. A function generator 12 serves to generate functions in the spatial frequency domain of the weighting function supplied to a Fourier transformer device 13. Suitable forms of the functions generated by the function generator 12 may comprise:

$$\hat{\phi}_1(\omega)=a|\omega|\exp(b|\omega|)$$

$$\hat{\phi}_2(\omega)=a|\omega|\exp(b\omega^2)$$

$$\hat{\phi}_3(\omega)=|\omega|(a+b\omega^2)$$

$$\hat{\phi}_4(\omega)=(a+b|\omega|+c\omega^2+\ldots)|\sin \beta\omega|$$

Figure 9:
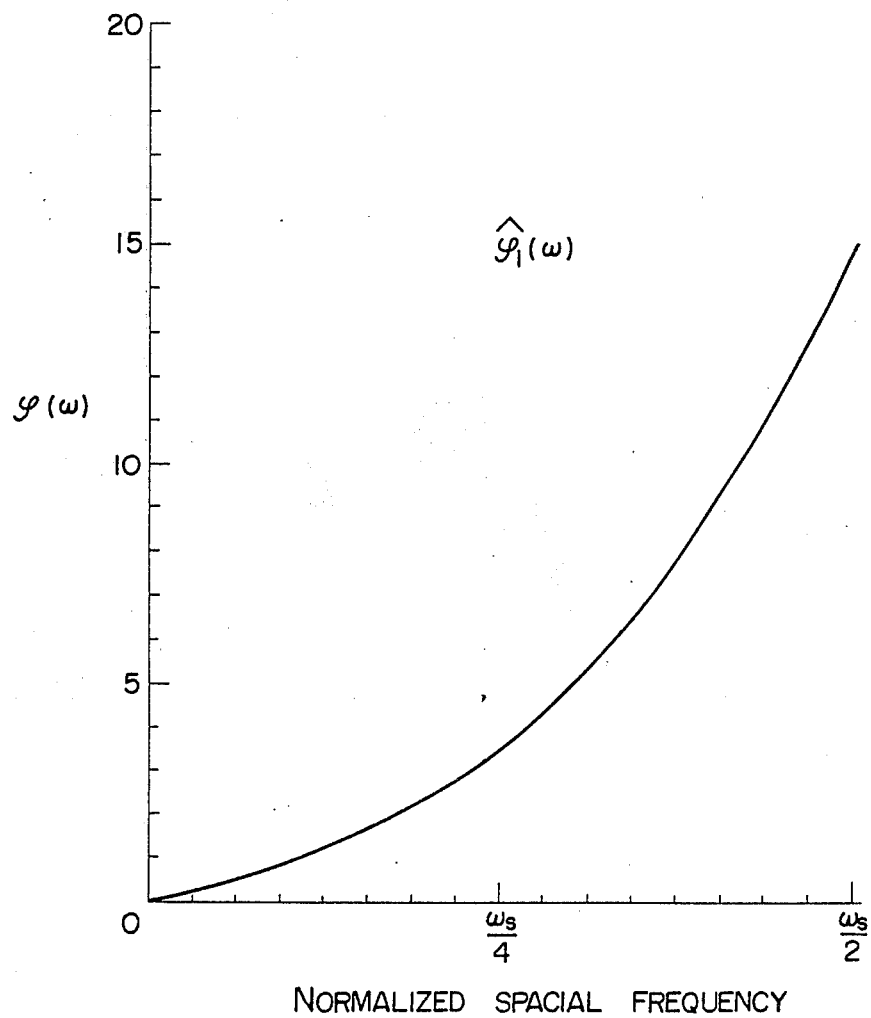
FIGS. 9 and 10 illustrate examples of forms of the weighting function, in the spacial frequency domain, which is used in the invention.
Figure 10:
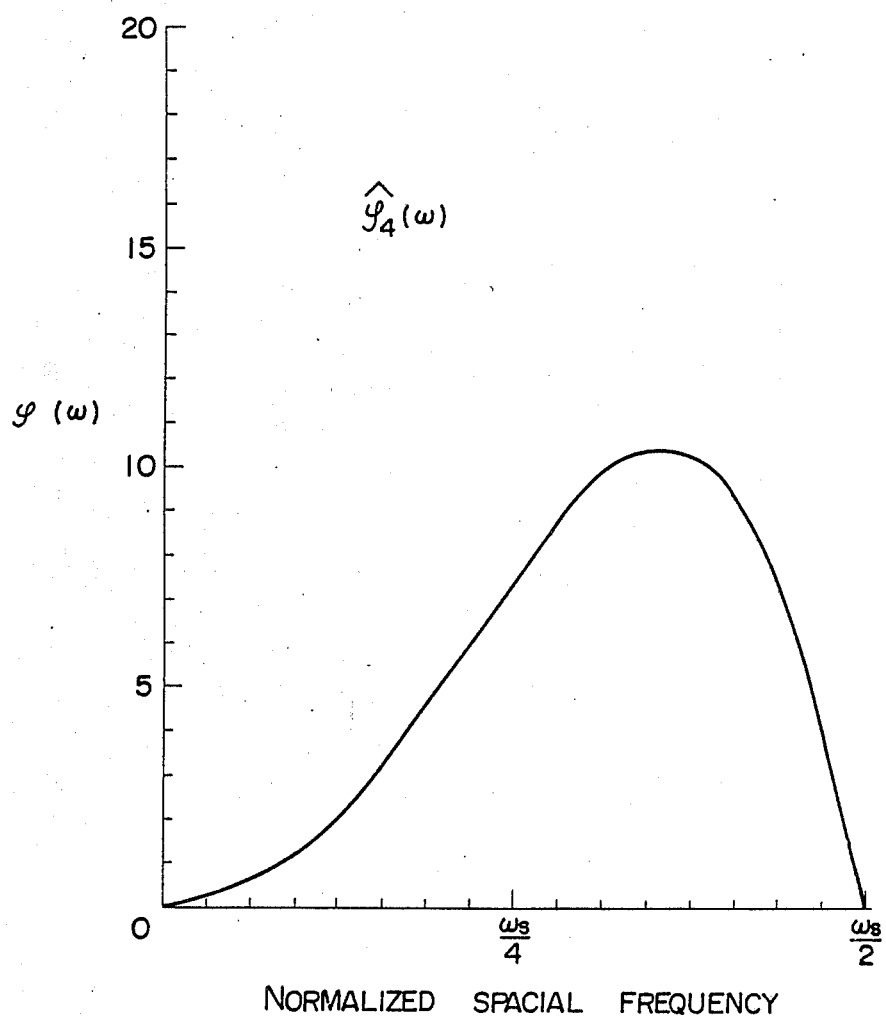

Examples of the functions $\hat{\phi}_1(\omega)$ and $\hat{\phi}_4(\omega)$ are graphically illustrated, respectively, in FIGS. 9 and 10, in which spacial frequency normalized by a sampling frequency is taken along the abscissa with values of $\hat{\phi}(\omega)$ taken along the ordinate. In more detail, when the sampling interval for an X-ray beam is represented by P mm, then the sampling frequency $f_s$ is given by $$f_s=(1/P)$$

since $\omega=2\pi f$, $$\omega_s=(2\pi/P)$$

The sampled data contain no frequency components higher than a half of the sampling frequency. Thus, the abscissa in these figures is scaled in the range of $\omega$ from 0 to $\omega_s/2$ under the condition that $P=1$. In FIG. 9, the constants a and b are selected to be equal to 1 and 0.5, respectively. In FIG. 10, the constants a, b, c and $\beta$ are selected to be equal to 1, while d and so forth are selected to be equal to zero. It will be seen from FIG. 9 that the function $\hat{\phi}(\omega)$ has a positive first-differential coefficient value at $\omega=0$ and the second differentiation is positive over the spacial frequency $\omega$. The same applies to the functions $\hat{\phi}_2(\omega)$ and $\hat{\phi}_3(\phi)$, although they are not illustrated. On the other hand, the function $\hat{\phi}_4(\omega)$ has a positive first-differential coefficient value at $\omega=0$, while the second differentiation is positive until a predetermined value of $\omega$ and the function decreases in the frequency range beyond the predetermined value.

The Fourier transform device 13 is destined to perform the inverse Fourier transform of the functions $\hat{\phi}(\omega)$ generated by the function generator 12. Since the functions $\hat{\phi}(\omega)$ generally contain no imaginary term, the inverse Fourier transforms of these function are effected through the same processing as the Fourier transforms. Thus, a conventional Fourier transformer device may be used. It will be appreciated that the function generator 12 may be replaced by a memory in which the functions $\hat{\phi}(\omega)$ are stored. The memory 14 serves to store the results of Fourier transforms of $\hat{\phi}(\omega)$, namely the weighting functions $\phi(t)$. A controller 15, which may be constituted by an electronic computer, supplies command signals to the Fourier transformer device 13 and a memory read-out controlling circuit 16. The memory read-out controlling circuit 16 produces control commands for reading out the projection data and the weighting functions from the memories 11 and 14 in predetermined sequences, and, at the same time, produces an operation command signal to a convolution processor 17. The convolution processor 17 is composed of a multiplication circuit, an adder circuit, and a memory, and performs an arithmetic operation of $\Sigma_j \phi_j P_{i+j}$ on the projection data $P_i$ and the weighting functions $\phi_j$. Results of this arithmetic operation are transferred to a memory 18 to be stored. Reconstruction of a cross-section image from the projection images can be accomplished through addition processing of data stored in the memory 18.

FIG. 8 is a block diagram showing an arrangement of the convolution processor 17. In the figure, reference numerals 81 and 82 denote memories which correspond to the memories 11 and 14. The memory 81 serves to store the projection data, while the memory 82 stores the weighting functions. A multiplier circuit 83 produces products of the data stored in the memories 81 and 82, which are added with contents stored in a memory 84 through an adder circuit 85. The added results are stored again in the memory 84. The latter thus has to be reset to zero at the initialization. For performing the convolution operation on the projection image data p(n, θ) by using a weighting function having five weights, operations of storing $p(n-2,\theta) \times \phi(1) = Q(1)$ in the memory 84 and storing $Q(1) + p(n-1,\theta) \times \phi(2) = Q(2)$ in the memory 84 have to be repeated five times. Thereafter, similar operations are repeated on the projection image p(n, θ) by varying the value of n.

It is self-explanatory that operations of the arithmetic operating circuitries of the Fourier transformer device 13 and the convolution processor 17 may be performed by a suitable electronic computer.

From the foregoing description, it will be appreciated that the method of reconstructing a cross-sectional image of an object from projection images thereof through the convolution process according to the teachings of the invention allows a sharp image to be obtained without blurs by using a weighting function that has a second differentiation which is positive in at least a predetermined range of the spacial frequency domain.

In the above discussion, it has been assumed that an X-ray is employed. However, the invention is not restricted to the use of X-rays, and other radiation rays such as γ-rays, can be used.

What is claimed is:

1. An apparatus for detecting an object by means of permeable radiation rays, comprising:
   irradiation source means for generating said permeable rays to irradiate said object therewith so that said radiation rays transmit through a planar cross-section of said object;
   detector means for detecting the radiation rays transmitted through said object to provide an electrical signal corresponding to plural blurred projection images of said cross-section depending upon the transmitted radiation rays;
   function generator means for generating an inverse Fourier transformed function including a correction factor for correction of the plural blurred projection images in that the function second differentiation is positive in at least a predetermined range of a spacial frequency domain and has a positive first-differential coefficient at a point where the spacial frequency is equal to zero; and
   convolution processor means for receiving said electrical signal from said detector means and said inverse Fourier transformed function from said function generator to perform a convolution integral operation on said electrical signal with said inverse Fourier transformed function used as a weighting function to reconstruct an unblurred three-dimensional image of the planar cross-section of said object.

2. An apparatus according to claim 1, wherein said inverse Fourier transformed function generated by said function generator has a function shape in which the values of said function decrease in a range of said spacial frequency domain other than said predetermined range.

3. An apparatus according to claim 2, wherein the range in which said function decreases is higher in frequency than said predetermined range.

4. An apparatus according to claim 1, wherein the irradiation source means irradiates the object from plural directions.

5. An apparatus for reconstructing an unblurred three-dimensional image of a planar cross-section of an object, comprising:
   irradiation source means for generating permeable rays having a predetermined amount of beam spreading of the rays to irradiate said object therewith so that said radiation rays transmit through a planar cross-section of said object;
   detector means for detecting the radiation rays transmitted through said object to provide an electrical signal corresponding to plural blurred projection images of said cross-section depending upon the transmitted radiation rays, wherein the blur of said projection images is caused by the beam spreading of the rays;
   function generator means for generating an inverse Fourier transformed function including a correction factor for correction of the plural blurred projection images in that the function second differentiation is positive in at least a predetermined range of a spacial frequency domain and which has a positive first-differential coefficient at a point where the spacial frequency is equal to zero; and
   convolution processor means for receiving said electrical signal from said detector means and said inverse Fourier transformed function from said function generator to perform a convolution integral operation on said electrical signal with said inverse Fourier transformed function used as a weighting function to compensate for the blurring caused by the beam spreading to reconstruct an unblurred three-dimensional image of the planar cross-section of said object.

6. An apparatus for detecting an object by means of permeable radiation rays, comprising:
   irradiation source means for generating said permeable rays to irradiate said object therewith so that said radiation rays transmit through a planar cross-section of said object;
   detector means for detecting the radiation rays transmitted through said object to provide an electrical signal corresponding to plural blurred projection images of said cross-section depending upon the transmitted radiation rays;
   first memory means for storing the output signal of said detector means; and
   an image reconstructing section for performing a convolution integral operation on the contents of said first memory means by means of a weighting function to reconstruct an unblurred three-dimensional image of the cross-section of said object, said image reconstructing section including first function generator means for generating a function whose second differential is positive in at least a predetermined range of a spacial frequency domain and which has a positive first-differential coefficient at a point where the spacial frequency is equal to zero, second function generator means for generating an inverse Fourier transform of the function generated by said first function generator means and used as said weighting function, second memory means for storing said inverse Fourier transformed function, control means for successively reading out the contents of said first and second memory means, and convolution processor means for performing multiplying and summing operations on the read-out contents of said first and second memory means.

7. An apparatus for detecting an object by means of permeable radiation rays, comprising:

irradiation source means for generating said permeable rays to irradiate said object therewith so that said radiation rays transmit through a planar cross-section of said object;

detector means for detecting the radiation rays transmitted through said object to provide an electrical signal corresponding to plural blurred projection images of said cross-section depending upon the transmitted radiation rays;

first memory means for storing the output signal of said detector means; and an image reconstructing section for performing a convolution integral operation on the contents of said first memory means by means of a weighting function to reconstruct an unblurred three-dimensional image of the cross-section of said object, said image reconstructing section including first function generator means for generating a function whose second differential is positive in at least a predetermined range of a spacial frequency domain and which has a positive first-differential coefficient at a point where the spacial frequency is equal to zero, said function having a function shape in which the values of said function decrease in a range of said spacial frequency domain other than said predetermined range, second function generator means for generating an inverse Fourier transform of the function generated by said first function generator means and used as said weighting function, second memory means for storing said inverse Fourier transformed function, control means for successively reading out the contents of said first and second memory means, and convolution processor means for performing multiplying and summing operations on the read-out contents of said first and second memory means.

* * * * *